United States Patent [19]

Williams

[11] Patent Number: 5,041,264
[45] Date of Patent: Aug. 20, 1991

[54] METHOD AND APPARATUS FOR DISINFECTING OBJECTS

[76] Inventor: Robert M. Williams, 705 Kenyon St., N.W., Washington, D.C. 20010

[21] Appl. No.: 252,522

[22] Filed: Oct. 3, 1988

[51] Int. Cl.$^5$ .............................................. A61L 2/16
[52] U.S. Cl. .................................... 422/28; 422/294; 206/210; 383/72
[58] Field of Search ...................... 422/28, 36, 37, 292, 422/294, 300; 206/210, 219, 438, 571, 484.2; 383/72, 101, 109, 113

[56] References Cited

U.S. PATENT DOCUMENTS

| | | | |
|---|---|---|---|
| 1,817,530 | 8/1931 | Spanel | 422/294 |
| 4,224,367 | 9/1980 | Scholle | 206/484.2 |
| 4,349,104 | 9/1982 | Hayes | 206/205 |
| 4,362,241 | 12/1982 | Williams | 206/210 |
| 4,446,967 | 5/1984 | Halkyard | 206/363 |

FOREIGN PATENT DOCUMENTS 0217667  4/1987  European Pat. Off. ............ 383/113

Primary Examiner—David L. Lacey
Assistant Examiner—William H. Beisner
Attorney, Agent, or Firm—Beveridge, DeGrandi & Weilacher

[57] ABSTRACT

Contaminated objects are disinfected in a device which has a cavity formed by a fluid impermeable wall, an opening which is sealable, an absorbent liner, and a dispensing conduit which extends around the perimeter of the device. Objects are placed in the cavity, the opening is sealed, and a disinfectant solution is introduced into the dispensing conduit. The disinfectant solution flows from outlets in the conduit into the absorbent liner so that the objects in the cavity are disinfected by the solution and its vapors.

5 Claims, 1 Drawing Sheet

METHOD AND APPARATUS FOR DISINFECTING OBJECTS

BACKGROUND OF THE INVENTION

This invention is directed to a disinfection apparatus and method which is particularly suited for use in the health care field.

Current medical practice involves the use of a large number of disposable objects including syringes, garments, surgical drapes, dressings, hemostats, cotton tip applicators, speculums and other such items. In the course of normal use, these objects often come into contact with individuals who have infectious diseases, thus raising a possibililty that infected objects may later transmit infections or diseases to new victims.

There is a significant need for a device and method which will reduce the risk of spreading infection by contact with contaminated disposable waste materials. The present invention provides a device and method which is relatively uncomplicated and quite effective for this purpose, and it is suitable for use in many locations including hospitals, physician's offices, dental offices, or homes.

SUMMARY OF THE INVENTION

The invention involves a device with a cavity for holding objects to be disinfected. The cavity is formed by a wall of sheet material which is substantially impervious to liquids and gases. The device has an opening which permits objects to be inserted into the cavity. An absorbent liner of sheet material is located inside the impervious wall where it will face toward objects placed in the cavity. A dispensing conduit extends around the perimeter of the device. Means are provided for introducing the disinfectant solution into the conduit, and the conduit has outlets which release the disinfectant solution into the absorbent liner. Sealing means are provided for closing the opening to retain the disinfectant solution in the cavity so that the objects placed therein will be disinfected by the solution and its vapors.

Preferably, the wall of the device is formed on laminated sheets of polyester and polyethylene, and the absorbent liner is a sheet of nonwoven fibrous material. Suitable disinfecting solutions include glutaraldehyde, an aqueous solution of sodium hypochlorite, an aqueous solution of isopropyl alcohol, an aqueous solution of ethanol alcohol, or a phenyl solution which may include glutaraldehyde.

The invention also involves a method of disposing of biological materials, contaminated items and other objects. This method is performed by placing such objects in the device described in the two preceding paragraphs, using the sealing means to close and seal the cavity, and introducing the disinfectant solution into the dispensing conduit so that it flows through the outlets around the perimeter of the device into the absorbent liner where the solution and its vapors will disinfect the contaminated objects in the device.

The invention may be practiced by a wide variety of devices. An exemplary version is described below and is illustrated in the accompanying drawings.

DETAILED DESCRIPTION

Figure 1:
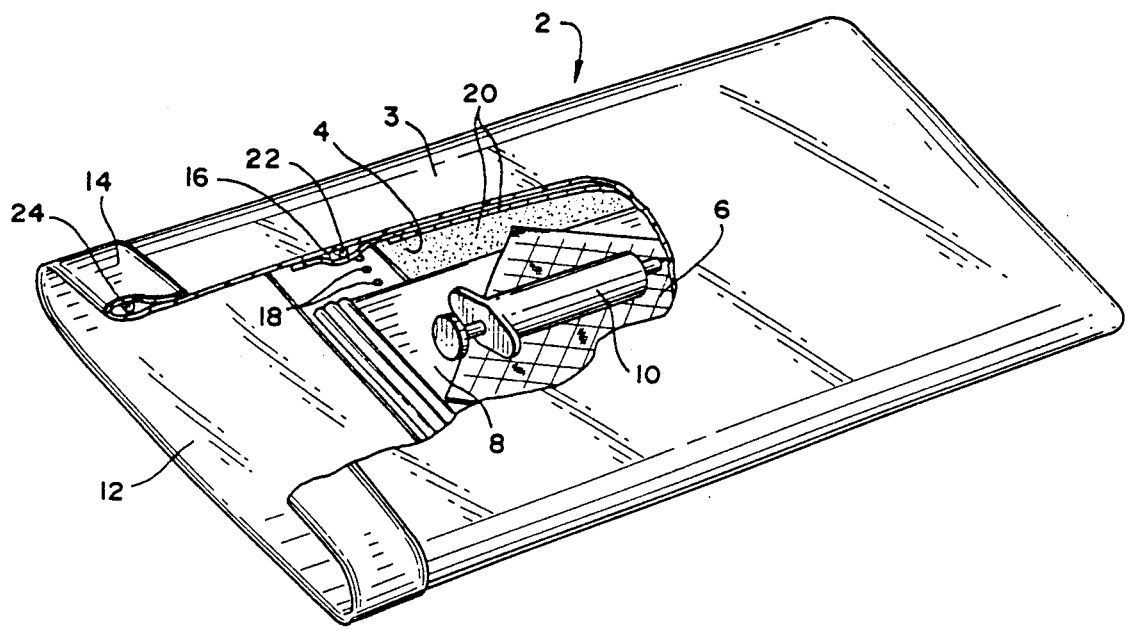
FIG. 1 is a broken perspective view showing the device according to the invention in a flat unsealed condition, with contaminated products having been inserted into the device prior to sealing.

Referring to FIG. 1, it will be seen that the device 2 is a flexible bag formed of a fluid impervious wall 3 of sheet material, the interior of which is a cavity 4 for receiving contaminated objects such as gauze 6, a used surgical drape 8, and a syringe 10. At the end of the device, there is an opening 12 through which contaminated objects are inserted into the cavity 4. Extending circumferentially around the opening 12, there is a hem 14 which contains a drawstring 24 which is used to constrict and close the opening as will be described later in this specification.

Spaced downwardly from the opening 12, the device has a dispensing conduit 16 which extends around the perimeter of the device. This conduit is formed by fusion bonding the spaced margin portions of an internal circumferential band of plastic material to the internal surface of the wall 3. This provides the space which forms the conduit 16. A plurality of outlet openings 18 are punched in the conduit 16 so that any disinfectant solution in the conduit will flow through the outlets 18 into the cavity of the device.

The interior of the cavity 4 is lined with an absorbent sheet material 20 which preferably is a hydrophilic nonwoven fabric which is well known in the art. The absorbent liner 20 preferably extends circumferentially around the cavity to line the entire wall portion which lies inwardly of the dispensing conduit.

A frangible ampule 22 which contains a disinfectant solution is located in the dispensing conduit 16. When the ampule is broken, the conduit distributes the liquid circumferentially around the cavity 4 so that it can flow through the outlets 18 into the absorbent liner material 20. When thus distributed, the disinfectant solution can contact the contaminated objects and it also vaporizes to provide a disinfecting gas which penetrates the objects to provide a thorough disinfecting action.

To enhance the disinfecting action and to contain any disinfecting solutions and vapors which have a high toxicity, the device is provided with means for sealing the opening 12. The sealing means may be a mechanical locking arrangement of the type used in plastic bags sold under the trademark ZIP-LOK, or it may be an adhesive coating which, prior to sealing, is covered by a sheet of release paper which prevents premature sealing. In the disclosed embodiment, however, the sealing means includes a drawstring 24 which is spaced a sufficient distance from the contents of the device so that the neck of the bag may be folded at 26 and tied in the manner shown diagrammatically in FIG. 2. The drawstring 24 is wrapped one or more times around the entire device at a point which lies between the fold 26 and the disinfectant conduit 16, pulled taut, and knotted at 28 to assure a hermetic seal.

Figure 3:
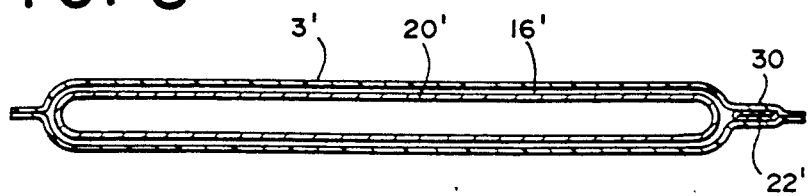

In an alternative embodiment of the invention shown in the transverse sectional view of FIG. 3, the dispensing conduit 16' is located on the exterior of the impermeable wall 3' of the bag. Here, the circumferential conduit-forming strip has portions 30 which protrude laterally from the bag to provide a chamber for the frangible ampule 22'. Such an arrangement makes it easier to find the ampule when the user wishes to break it to release the disinfectant solution into the dispensing conduit, absorbent liner 20′, and the contents of the device.

Figure 2:
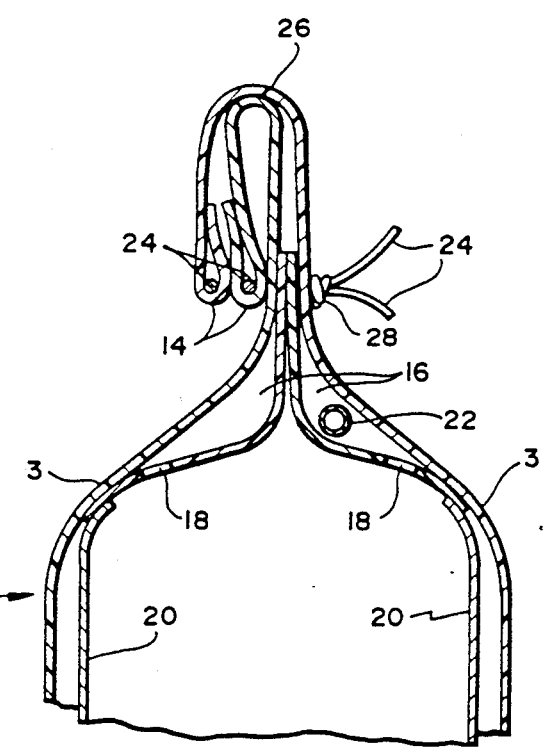
FIG. 2 is a diagrammatic sectional view showing the device in a sealed condition; and, FIG. 3 is a transverse sectional view showing a modified version of the device.

The device of the invention can be used as a wastebasket liner, a hanging receptacle, or it may be kept in a drawer, on a shelf or in some other storage location until it is called into use. In any event, contaminated objects such as gauze, syringes or dressings are placed in the device, and the drawstrings 24 is pulled to constrict and close the opening 12. To assure that the seal is complete, the constricted neck is folded and gathered as shown in FIG. 2, and the ends of the drawstring 24 are wrapped around the entire neck and tied so that vapors cannot escape from the device. Then, the user breaks the ampule. The released disinfectant solution will then flow circumferentially around the bag in the distribution conduit, and then flow through the outlets 18 into the bag contents and absorbent liner. The disinfectant liquid and its vapors will then disinfect the bag contents so that the entire package can be disposed of without risk of contaminating persons who come into contact with it.

A variety of materials are suitable for forming the wall 3 of the bag, but it is important that such materials be impervious to fluids including liquid and gas. A preferred material of this nature is a bag formed of laminated sheet material having a layer of polyester adhesively bonded to a layer of polyethylene. The polyester has a 48 gage thickness, and the polyethylene has a thickness of 1.5 mil, thus providing a total thickness of approximately 2 to 3 mils. Such a product is available from Jaite Packaging, Inc., Akron, Ohio 44313. Other suitable bags can be formed of polyethylene or polyester with metallized foil layers thereon to obstruct the escape of liquids and vapors from the cavity 4 of the device.

The disinfectant solution is preferably glutaraldehyde. Alternatively, the disinfectant may be (1) a 5.25% aqueous solution of sodium hypochlorite, a 70% aqueous solution of isopropyl alcohol, an aqueous solution of 70% ethanol alcohol, or a phenyl based solution which may include glutaraldehyde.

The closed device, due to the high concentration of fumes from the solution, is lethal to organisms, spores, bacteria, viruses and fungi.

Although the preferred forms of the invention have been illustrated, it may take various other forms. For example, the disinfectant solution can be introduced at a lower area in the device so that the liquid will, by capillary action wick upwardly to impregnate the liner. Devices other than frangible ampules can be used to release the disinfectant solution into the distribution conduit, and a variety of other sealing means may be used. In view of these possible variations, it is emphasized that the invention is not limited only to the disclosed embodiments but embraces a wide variety of devices and methods which fall within the spirit of the following claims.

I claim:

1. A device for receiving and disinfecting biological materials, contaminated items, and other objects, comprising,
   a wall which forms a cavity for holding objects to be disinfected, said wall being formed of a sheet material which is substantially impervious to liquids and gases,
   an absorbent liner of sheet material which is located inside the wall so as to face toward objects in the cavity,
   a dispensing conduit means for releasing disinfectant solution into said absorbent liner, said dispensing conduit means extending around the perimeter of the device and having outlets which are positioned around the perimeter of the device to release disinfectant solution into said absorbent liner,
   means for introducing a disinfectant solution into the dispensing conduit means so that the disinfectant solution will be released through said outlets into said absorbent liner,
   said device having an opening which permits objects to be inserted into the cavity, and sealing means for closing the opening to retain objects and disinfectant solution within the cavity so that the objects will be disinfected by the disinfectant solution and its vapors.

2. A device according to claim 1 wherein the sealing means includes a drawstring which extends around the opening to constrict and close the opening, said wall being folded on itself between the drawstring and the dispensing conduit, said drawstring also extending around the device at a location between the fold and the dispensing conduit.

3. A device according to claim 1 wherein the means for introducing a disinfectant solution is a frangible ampule.

4. A device according to claim 1 wherein the wall is formed of layers of polyethylene and polyester.

5. A method of disinfecting biological materials, contaminated items, and other objects, comprising the steps of,
   providing a device which has a wall which forms a cavity for holding objects to be disinfected, said wall being formed of sheet material which is substantially impervious to liquids and gases, said device having an opening which permits objects to be inserted into the cavity, and an absorbent liner of sheet material which is located inside the wall so as to face toward objects in the cavity, said device having a dispensing conduit which extends around the perimeter of the device and has outlets formed therein,
   inserting contaminated objects into said cavity,
   closing the opening with a sealing means,
   introducing a disinfectant solution into the dispensing conduit means so that liquid flows around the perimeter of the device, and releasing the disinfectant solution around the perimeter of the device through said outlets into said absorbent liner, and retaining the objects in the device until objects are disinfected by the disinfectant solution and its vapors.

* * * * *